(12) United States Patent
Clynes (10) Patent No.: US 6,413,937 B1
(45) Date of Patent: Jul. 2, 2002

(54) COMBINATIONS FOR USE IN INCREASING THE POTENCY OF A SUBSTRATE FOR MULTIDRUG RESISTANCE RELATED PROTEIN

(75) Inventor: Martin Michael Clynes, Clontarf (IE)

(73) Assignee: Dublin City University and Enterprise Ireland, Dublin (IE)

( * ) Notice: Subject to any disclaimer, the term of this patent is extended or adjusted under 35 U.S.C. 154(b) by 0 days.

(21) Appl. No.: 09/297,329

(22) PCT Filed: Oct. 24, 1997

(86) PCT No.: PCT/IE97/00071
§ 371 (c)(1),
(2), (4) Date: Apr. 29, 1999

(87) PCT Pub. No.: WO98/18490
PCT Pub. Date: May 7, 1998

(30) Foreign Application Priority Data

Oct. 31, 1996 (IE) .................................................. 960761

(51) Int. Cl.$^7$ ........................ A01N 43/04; A61K 31/70; C07D 209/26
(52) U.S. Cl. ............................ 514/34; 514/25; 548/500
(58) Field of Search ....................... 514/25, 34; 548/500

(56) References Cited

U.S. PATENT DOCUMENTS 4,208,414 A    6/1980   Schinitsky
5,567,592 A  * 10/1996   Benet et al. ................. 435/7.21

FOREIGN PATENT DOCUMENTS

EP        A20334576      9/1989

OTHER PUBLICATIONS

Endicott et al., Annual Review of Chem., vol. 58, pp. 137–171, 1989.*
E.B. Polevaya et al, Sov.Med., No. 8, 1987, pp. 27–30.
R.D. Maca, Anticancer Drug Design, vol. 6, 1991, pp. 453–466.
Jose Saban et al, Am.J.Clin. Path., vol. 86, No. 2, 1986, pp. 241–247.
Eva Hofsli et al, Cancer Res., vol. 50, No. 13, 1990, pp. 3997–4002.
Zsolt Hollo et al, Febs Letters, vol. 383, No. 1–2, 1996, pp. 99–104.
Enrico Mihich et al, Forum Trends in Experimental and Clinical Medicine, vol. 4, No. 3, 1994, pp. 290–304.
Gabriele Jedlitschky et al., Cancer Research, vol. 56, Mar. 1, 1996, pp. 988 to 994.
S. P. C. Cole et al., Science, vol. 258, Dec. 4, 1992, pp. 1650–1654.
Martin Clynes, In Vitro Cell. Dev. Biol., vol. 29A, Mar. 1993, pp. 171–179.
Gary D. Kruh et al., Journal of The National Cancer Institute, vol. 87, No. 16, Aug. 16, 1995, pp. 1256–1258.
Paul Saptarshi et al., Proc. Natl. Acad. Sci. USA, vol. 93, Jul. 1996, pp. 6929–6934.

* cited by examiner

*Primary Examiner*—Gary Geist
*Assistant Examiner*—Howard V. Owens, Jr.
(74) *Attorney, Agent, or Firm*—Birch, Stewart, Kolasch & Birch, LLP (57) ABSTRACT

A combination of an agent which is a substrate for multidrug resistance related protein (MRP) and an inhibitor of MRP which is a nonsteroidal anti-inflammatory drug (NSAID) or a structural analogue thereof for simultaneous, sequential or separate use for increasing the potency of the substrate. The substrates include anti-cancer drugs and transition metal complexes. The combinations can be used to overcome the resistance to MRP substrates exhibited in many conditions, such as resistance to chemotherapy where patients have developed resistance, especially as a result of MRP over-expression to their chemotherapy.

13 Claims, 5 Drawing Sheets

COMBINATIONS FOR USE IN INCREASING THE POTENCY OF A SUBSTRATE FOR MULTIDRUG RESISTANCE RELATED PROTEIN

This application is the national phase under 35 U.S.C. §371 of PCT International Application No. PCT/IE97/00071, which has an international filing date of Oct. 24, 1997, which designated the United States of America.

TECHNICAL FIELD

This invention relates to combinations of active substances for use in increasing the potency of a substrate for multidrug resistance related protein.

BACKGROUND ART

MRP (multidrug resistance related protein) is a large molecular weight glycoprotein which uses ATP as an energy source and is responsible for the efflux of a specific range of drugs. Other names for MRP are multidrug resistance protein and multidrug resistance associated protein. MRP was discovered because of its over-expression in a number of multidrug resistant human tumour cell lines that do not over-express the MDR1 P-glycoprotein (Cole, S. P. C., et al., (1992); Science (Washington D.C.), 258: 1650–1654). MRP is found in normal human cells, including muscle, kidney and testicular tissue, but levels have been shown to be elevated in many cancer cell lines (Kruh G. D., et al. (1995) Journal of the National Cancer Institute; 87, 16: 1256–1258). The spectrum of substances (including anti-cancer agents) affected by MRP has been broadly defined and includes both non-metabolised anti-cancer agents, such as vincristine (Paul, S., et al., (1996) Proceedings of the National Academy of Science, 93: 6929–6934), and substances possessing a glutathione, glucuronide or sulfate group following cellular metabolism (Jedlitschky, G., et al., (1996) Cancer Research, 56: 988–994). In this way a one or a two-step process may be responsible for the efflux of a particular MRP substrate; an ATP dependent pumping of the agent alone, as is the case with certain anti-cancer agents, including vincristine, or a metabolic conversion followed by the pumping action of MRP, as is seen with glucuronosyl etoposide.

Human cancers have the ability to generate variants resistant to many of the commonly-used chemotherapeutic agents. Combination chemotherapy was introduced to overcome this problem, but variants can arise that are cross-resistant to different sets of drugs; often the drugs within the same set are structurally very different and may act in the cell by totally distinctive mechanisms. Understanding the molecular basis for multidrug resistance (MDR) is an important challenge for cancer research (Clynes, M., (1993) In Vitro Cell. Dev. Biol. 29A: 171–179).

An important goal of experimental chemotherapy research is to identify compounds which, at safe doses, can circumvent drug resistance (Clynes, M. (1993) supra).

Thus, there is a constant search for combinations of drugs for use in chemotherapy so as to circumvent the problem of multidrug resistance. In particular, there is a need for chemotherapeutic agents which can increase the cancer cell killing potency of anti-cancer drugs by inhibiting the various cellular multidrug resistance mechanisms.

The possibility of increasing the activity of etoposide (VP-16) by combining this anti-cancer agent with indomethacin has been investigated by treating murine and human cultured tumour cells with a combination of indomethacin and VP-16 (Maca, R. D. (1991), Anti-Cancer Drug Design 6: 453–466). Maca showed that non-toxic concentrations of indomethacin enhanced the VP-16 sensitivity of a variety of cancer cell lines, and the methotrexate sensitivity of one cancer cell line in vitro. This toxicity enhancement effect with VP-16 was assumed to be due to an increase in the accumulation of VP-16. Non-steroidal anti-inflammatory drugs (NSAIDs) other than indomethacin were not investigated. Furthermore, there is no indication from the results obtained that the effect is seen only with anti-cancer drugs which act as substrates for MRP and with NSAIDs which are of a suitable chemical nature.

DISCLOSURE OF INVENTION

The invention provides a combination of an agent which is a substrate for multidrug resistance related protein (MRP) and an inhibitor of MRP which is a non-steroidal anti-inflammatory drug (NSAID) or a structural analogue thereof for simultaneous, sequential or separate use for increasing the potency of said substrate.

Use of a combination of a substrate for MRP and an inhibitor of MRP in accordance with the invention has the potential to overcome the resistance to such substrates exhibited in many conditions, such as resistance to chemotherapy where patients have developed resistance (especially via MRP overexpression to their chemotherapy).

Preferably, the substrate is an anti-cancer drug.

Anti-cancer drugs are also referred to herein as chemotherapeutic drugs.

When the substrate is an anti-cancer drug, the anti-cancer drug is preferably selected from an anthracycline, a vinca alkaloid and an epipodophyllotoxin.

A suitable anthracycline is adriamycin, (also known as doxorubicin), daunorubicin or epirubicin.

A suitable vinca alkaloid is vincristine.

A suitable epipodophyllotoxin is etoposide (VP-16) or teniposide.

Thus, in one embodiment the invention provides a way of increasing the cytotoxic effect of particular anti-cancer drugs by blocking cellular resistance based on MRP.

However, the substrate can also be a transition metal complex, more especially a positive transition metal complex.

When the inhibitor is a structural analogue of an NSAID the structural analogue will normally be derived from an NSAID.

Further, preferably, the NSAID is a heteroarylacetic acid. Suitable heteroarylacetic acids are acemetacin, indomethacin, sulindac, sulindac sulfide, sulindac sulfone, tolmetin and zomepirac.

Alternatively, the NSAID is a non-heteroarylacetic acid compound such as the fenamic acid mefenamic acid.

We have found that the cancer killing effect of several anti-cancer drugs is greatly increased by concurrent administration of non-toxic doses of specific NSAIDs belonging primarily to the heteroarylacetic acid sub-group.

We have found that drugs from other anti-cancer classes, including anti-metabolites, alkylating agents, topoisomerase and microtubule inhibitors do not produce the effects observed with the combinations according to the invention.

As indicated above, preferred inhibitors of MRP are heteroarylacetic acids. These are typically NSAIDs. However, the mechanism whereby heteroarylacetic acids cause their toxicity enhancement effect in accordance with the invention is separate from the mechanism by which NSAIDs are assumed to carry out their therapeutic actions i.e., inhibition of cyclooxygenase enzyme activity. Although not wishing to be bound by any theoretical explanation of the invention, it would appear that the mechanism of toxicity enhancement is dependent on the NSAID fulfilling stringent structural criteria.

The heteroarylacetic acid NSAIDs indomethacin, sulindac and tolmetin as well as the indomethacin analogue acemetacin and the tolmetin analogue zomepirac have been found to enhance the toxicity of MRP-specific substrates. Acemetacin is believed to be a pro-drug of indomethacin and is converted in the liver to the therapeutically active product indomethacin. As we have found that acemetacin is found to be active as a toxicity enhancing agent in vitro in both leukemia and lung cancer cells, where the conversion to indomethacin should not occur, it is clear that the mechanism whereby these compounds cause their toxicity enhancement effect is other than by the mechanism by which NSAIDs are assumed to carry out their therapeutic actions as indicated above.

As evidence that the MRP inhibitor for use in accordance with the invention must meet stringent structural criteria the fact that etodolac, which also belongs to the heteroarylacetic acid group of NSAIDs, does not exhibit the enhanced cytotoxicity observed with other members of this group, as hereinafter described and exemplified.

Mefenamic acid is a fenamic acid NSAID which can be used to enhance the cytotoxicity of MRP substrates in accordance with the invention. However, no additional members of the fenamic acid NSAID chemical class have been shown to enhance toxicity. The fact that close structural analogues of mefenamic acid do not have the ability to enhance MRP substrate toxicity illustrates the extent of the stringency of the structural requirements required for the enhancement of the toxicity of MRP specific substrates.

The following examples demonstrate that the combinations in accordance with the invention have an enhanced toxicity effect. This increased toxicity or cell kill would be expected to kill more tumour cells either totally eliminating cancers (i.e. a cure) or lengthening the time of remission from the effects of the cancer.

It is also expected that the combination in accordance with the invention might broaden the spectrum of cancers treatable with a particular anti-cancer agent.

It is also anticipated that the combination in accordance with the invention would be less sensitive to the evolution of chemotherapeutic drug resistance over time, since fewer cells would survive to produce resistant populations.

Since a given dose of anti-cancer drug would have a greater effect in the combination therapy according to the invention, it would be expected that a reduction in the total dose of chemotherapeutic agent would be possible, thereby reducing the toxic side effects of the treatment.

Resistance to pentavalent arsenicals and trivalent antimonials, as exhibited by *Leishmania tropica* (a unicellular eukaryotic parasite that causes cutaneous leishmaniasis, oriental sore, in man) is one possible non-cancer disease which might be circumvented by MRP inhibition in accordance with the invention.

However, it is anticipated that other agents, such as antifungal agents, antiparasitic agents, etc. may have their efficacy enhanced when combined with an MRP inhibitor in accordance with the invention.

As regards the use of heteroarylacetic acids as the MRP inhibitor in accordance with the invention, it is known that certain side effects of cancer and the chemotherapeutic drugs used to treat it are caused by prostaglandins. Since all heteroarylacetic acids known to be effective are inhibitors of prostaglandin synthesis, it is reasonable to expect that there would be a reduction in the prostaglandin effects from the chemotherapy.

The substrate for and the inhibitor of MRP for use in accordance with the invention will be administered to a human or animal subject in any form typically used for its administration. Thus, the two components can be administered orally, parenterally or in any other way to achieve the desired effects.

The invention will be further illustrated by the following Examples.

MODES FOR CARRYING OUT THE INVENTION

EXAMPLE 1

This Example shows the effect of combining a substrate for MRP with an inhibitor of MRP in accordance with the invention. In each case, the substrate for MRP was an anti-cancer drug or a transition metal complex (example vii only) and the inhibitor was an NSAID.

The cell lines used were DLKP, A549 and OAW42-SR cell lines.

DLKP and A549 are both human lung carcinoma cell lines. The DLKP and DLKP-A cell lines were derived on site as primary cultures. A549 was obtained from the European Collection of Animal Cell Cultures (ECACC), Porton Down, Salisbury, U.K. The OAW42-SR is a heterogenous cell population derived by serial subculture of OAW42 (a cell line derived from the ascites of a patient with cystadenocarcinoma of the ovary, originally obtained from ECACC).

All the NSAIDs used in this Example and in the following Examples were supplied in solid form by the Sigma Chemical Company Ltd., Fancy Road, Poole, Dorset, BH12 4QH, England. The sulindac derivatives:—sulindac sulfone and sulindac sulfide were synthesised on site.

Adriamycin was obtained from Farmitalia; 5-flurouracil was obtained from David Bull Labs; etoposide (VP-16) and vincristine were obtained from Bristol-Myers Squibb Pharmaceuticals Ltd. The drugs were all supplied as solutions and were diluted for use in culture medium.

Potassium antimonyl tartrate was obtained from Sigma Chemical Company.

All the results presented in this Example for the DLKP, A549 and OAW42-SR cell lines were derived using the same miniaturised in vitro calorimetric assay system. On Day 1 of the assay 1000 cells/well/100 µl were plated into 96-well plates. Cells were allowed to attach overnight and cell viability was visually assessed. On Day 2 the two drugs (i.e. NSAID plus chemotherapeutic drug) to be analysed were added onto the cells. The individual drugs were added separately in 50 µl quantities (4× stocks, to take into account the dilution effect of having 200 µl final volume in each well). The drugs were left on the cells for five further days (Day 7) and cell number was determined using the acid phosphatase end-point assay which uses p-nitrophenol phosphate as substrate (Martin, A. and Clynes, M. (1991) *In Vitro Dev. Biol.*, 27A, 183–184). On Day 7 the culture medium was removed from the cells and they were washed once with phosphate buffered saline (PBS). After washing, 100 µl of freshly prepared substrate-containing buffer (0.1% Triton X-100 in 0.1M sodium acetate, pH 5.5) was added to each well and the plates were left in an incubator at 37° C. for 2 h. After the incubation period 50 µl of 1N NaOH was added to each well to develop the colour. The plates were then read at 405 nm (reference 620 nm) on an ELISA plate-reader.

In the results given below the % cell survival in the drug-free control is 100%. All results are the cell survival means ±S.D. from a minimum of three experiments. The NSAID concentrations in all cases are non-toxic i.e. there was no expectation of significantly increasing cell death by combining the two drugs.

In the following:

i), ii) and iii) are examples of a positive NSAID with a positive chemotherapeutic drug;

iv) is an example of a positive NSAID plus a negative drug;

v) is an example of a positive NSAID plus a positive drug on a P-170 overexpressing cell line: DLKP-A;

vi) is an example of a positive NSAID plus a positive drug on a LRP overexpressing cell line: OAW42-SR;

vii) is an example of a heavy metal plus sulindac on DLKP;

viii)–xv) represent results obtained with adriamycin and positive NSAIDs/NSAID-derived compounds; and xvi) is an example of adriamycin with a negative NSAID.

i) Adriamycin and Tolmetin (DLKP Cell line)

| | |
|---|---|
| Adriamycin (Adr)(10 ng/ml) | 60.35 ± 3.2 |
| Tolmetin (Tol)(25 µg/ml) | 100.49 ± 7.3 |
| Adr + Tol (25 µg/ml) | 16.78 ± 1.3 |
| Tolmetin (12.5 µg/ml) | 104.23 ± 6.2 |
| Adr + Tol (12.5 µg/ml) | 27.02 ± 3.0 |
| Tolmetin (6.25 µg/ml) | 104.38 ± 6.8 |
| Adr + Tol (6.25 µg/ml) | 40.75 ± 4.7 | ii) Vincristine and Sulindac (DLKP cell line)

| | |
|---|---|
| Vincristine (Vinc)(1.0 ng/ml) | 72.98 ± 3.5 |
| Sulindac (Sul)(6 µg/ml) | 114.1 ± 3.9 |
| Vinc + Sul (6 µg/ml) | 13.68 ± 0.8 |
| Sulindac (3 µg/ml) | 108.45 ± 10.6 |
| Vinc + Sul (3 µg/ml) | 23.23 ± 1.8 |
| Sulindac (1.5 µg/ml) | 111.6 ± 9.7 |
| Vinc + Sul (1.5 µg/ml) | 40.50 ± 4.4 | iii) VP-16/Etoposide and Sulindac (DLKP cell line)

| | |
|---|---|
| VP-16 (100 ng/ml) | 63.46 ± 1.4 |
| Sulindac (6 µg/ml) | 90.75 ± 3.3 |
| VP-16 + Sul 6 µg/ml | 18.82 ± 1.7 |
| Sulindac (3 µg/ml) | 93.68 ± 2.0 |
| VP-16 + Sul (3 µg/ml) | 24.24 ± 1.6 |
| Sulindac (1.5 µg/ml) | 95.07 ± 1.6 |
| VP-16 + Sul (1.5 µg/ml) | 38.18 ± 1.8 | iv) 5-Flurouracil (FU) and Sulindac (DLKP cell line)

| | |
|---|---|
| 5-FU (0.5 µg/ml) | 66.18 ± 1.4 |
| Sulindac (6 µg/ml) | 93.61 ± 5.9 |
| 5-FU + Sul (6 µg/ml) | 64.25 ± 6.2 |
| Sulindac (3 µg/ml) | 98.79 ± 8.8 |
| 5-FU + Sul (3 µg/ml) | 66.48 ± 7.1 |
| Sulindac (1.5 µg/ml) | 99.70 ± 7.7 |
| 5-FU + Sul (1.5 µg/ml) | 70.40 ± 6.2 | v) Vincristine and Sulindac (DLKP-A cell line)

| | |
|---|---|
| Vincristine (1.0 µg/ml) | 89.12 ± 1.3 |
| Sulindac | 105.7 ± 5.2 |
| Vinc + Sul (6 µg/ml) | 87.27 ± 5.2 |
| Sulindac (3 µg/ml) | 86.30 ± 13.7 |
| Vinc + Sul (3 µg/ml) | 90.71 ± 4.2 |
| Sulindac (1.5 µg/ml) | 108.9 ± 8.0 |
| Vinc + Sul (1.5 µg/ml) | 96.48 ± 7.4 | vi) Adriamycin and Indomethacin (Indo)(OAW42-SR cell line)

| | |
|---|---|
| Adriamycin (147 ng/ml) | 47.41 ± 1.3 |
| Indo (2.5 µg/ml) | 95.60 ± 3.3 |
| Adr + Indo (2.5 µg/ml) | 42.28 ± 1.6 |
| Indo (1.25 µg/ml) | 97.67 ± 1.3 |
| Adr + Indo (1.25 µg/ml) | 44.40 ± 3.1 |
| Indo (0.625 µg/ml) | 99.26 ± 3.7 |
| Adr + Indo (0.625 µg/ml) | 44.77 ± 3.2 | vii) Potassium Antimonyl Tartrate (PAT) and Sulindac (DLKP cell line)

| | |
|---|---|
| Potassium Antimonyl Tartrate (1.5 µg/ml) | 39.98 ± 3.3 |
| Sul (6.0 µg/ml) | 94.23 ± 1.2 |
| PAT + Sul (6.0 µg/ml) | 9.91 ± 0.9 |
| Sul (3.0 µg/ml) | 99.99 ± 2.9 |
| PAT + Sul (3.0 µg/ml) | 14.76 ± 0.8 |
| Sul (1.5 µg/ml) | 96.51 ± 5.3 |
| PAT + Sul (1.5 µg/ml) | 19.41 ± 2.6 | viii) Adriamycin and Acemetacin (A549 cell line)

| | |
|---|---|
| Adriamycin (15 ng/ml) | 61.00 ± 5.05 |
| Acemetacin (Ace)(37.50 µg/ml) | 85.04 ± 10.13 |
| Adr + Ace (37.50 µg/ml) | 19.25 ± 1.80 |
| Acemetacin (19.20 µg/ml) | 97.30 ± 8.46 |
| Adr + Ace (19.20 µg/ml) | 25.73 ± 2.65 |
| Acemetacin (11.50 µg/ml) | 102.08 ± 8.76 |
| Adr + Ace (11.50 µg/ml) | 30.66 ± 3.82 | ix) Adriamycin and Indomethacin (A549 cell line)

| | |
|---|---|
| Adriamycin (40 ng/ml) | 54.00 ± 6.05 |
| Indomethacin (2.40 µg/ml) | 92.18 ± 7.09 |
| Adr + Indo (2.40 µg/ml) | 21.00 ± 3.56 |
| Indomethacin (1.20 µg/ml) | 87.54 ± 13.07 |
| Adr + Indo (1.20 µg/ml) | 23.20 ± 4.25 |
| Indomethcin (0.60 µg/ml) | 92.38 ± 13.30 |
| Adr + Indo (0.60 µg/ml) | 25.48 ± 2.99 | x) Adriamycin and Mefenamic acid (A549 cell line)

| | |
|---|---|
| Adriamycin (15 ng/ml) | 47.00 ± 5.15 |
| Mefenamic acid (Mef)(7.90 µg/ml) | 85.23 ± 7.80 |
| Adr + Mef (7.90 µg/ml) | 14.92 ± 1.58 |
| Mefenamic acid (4.00 µg/ml) | 95.38 ± 9.21 |
| Adr + Mef (4.00 µg/ml) | 23.90 ± 2.55 |
| Mefenamic acid (2.30 µg/ml) | 98.49 ± 7.66 |
| Adr + Mef (2.30 µg/ml) | 24.66 ± 3.28 | xi) Adriamycin and Sulindac (A549 cell line)

| | |
|---|---|
| Adriamycin (40 ng/ml) | 46.00 ± 5.05 |
| Sulindac (6.30 µg/ml) | 96.01 ± 5.36 |
| Adr + Sul (6.30 µg/ml) | 27.14 ± 3.64 |
| Sulindac (3.20 µg/ml) | 101.00 ± 12.14 |
| Adr + Sul (3.20 µg/ml) | 27.72 ± 4.57 |
| Sulindac (1.50 µg/ml) | 100.00 ± 13.20 |
| Adr + Sul (1.50 µg/ml) | 28.50 ± 5.17 |

-continued

| xii) Adriamycin and Sulindac sulfide (A549 cell line) | |
|---|---|
| Adriamycin (15 ng/ml) | 70.67 ± 4.25 |
| Sulindac sulfide (6.00 µg/ml) | 90.19 ± 9.63 |
| Adr + Sul sulfide (6.00 µg/ml) | 26.79 ± 1.99 |
| Sulindac sulfide (2.70 µg/ml) | 104.91 ± 5.57 |
| Adr + Sul sulfide (2.70 µg/ml) | 34.80 ± 2.39 |
| Sulindac sulfide (1.40 µg/ml) | 105.83 ± 6.50 |
| Adr + Sul sulfide (1.40 µg/ml) | 26.74 ± 1.76 |
| xiii) Adriamycin and Sulindac sulfone (A549 cell line) | |
| Adriamycin (15 ng/ml) | 68.00 ± 5.82 |
| Sulindac sulfone (19.50 µg/ml) | 76.77 ± 6.49 |
| Adr + Sul sulfone (19.50 mg/ml) | 22.16 ± 1.78 |
| Sulindac sulfone (8.90 µg/ml) | 102.21 ± 8.88 |
| Adr + Sul sulfone (8.90 µg/ml) | 26.60 ± 2.87 |
| Sulindac sulfone (4.50 µg/ml) | 101.87 ± 10.52 |
| Adr + Sul sulfone (4.50 µg/ml) | 36.67 ± 10.52 |
| xiv) Adriamycin and Tolmetin (A549 cell line) | |
| Adriamycin (20 ng/ml) | 78.04 ± 3.95 |
| Tolmetin (24.20 µg/ml) | 99.24 ± 10.35 |
| Adr + Tolmetin (24.20 µg/ml) | 31.82 ± 2.73 |
| Tolmetin (14.10 µg/ml) | 97.59 ± 9.85 |
| Adr + Tolmetin (14.10 µg/ml) | 38.83 ± 3.07 |
| Tolmetin (8.50 µg/ml) | 91.84 ± 10.99 |
| Adr + Tolmetin (8.50 µg/ml) | 44.66 ± 3.13 |
| xv) Adriamycin and Zomepirac (A549 cell line) | |
| Adriamycin (15 ng/ml) | 89.01 ± 11.95 |
| Zomepirac (Zom)(38.80 µg/ml) | 94.89 ± 13.91 |
| Adr + Zom (38.80 µg/ml) | 24.58 ± 1.41 |
| Zomepirac (20.70 µg/ml) | 96.79 ± 12.10 |
| Adr + Zom (20.70 µg/ml) | 30.35 ± 2.85 |
| Zomepirac (11.40 µg/ml) | 105.94 +/ 13.000 |
| Adr + Zom (11.40 µg/ml) | 40.55 ± 3.45 |
| xvi) Adriamycin and Ibuprofen (A549 cell line) | |
| Adriamycin (17 ng/ml) | 76.70 ± 5.40 |
| Ibuprofen (Ibu)(15.72 µg/ml) | 95.58 ± 8.50 |
| Adr + Ibu (15.72 µg/ml) | 70.40 ± 7.59 |
| Ibuprofen (7.92 µg/ml) | 96.78 ± 11.43 |
| Adr + Ibu (7.92 µg/ml) | 69.75 ± 5.38 |
| Ibuprofen (3.06 µg/ml) | 100.37 ± 7.94 |
| Adr + Ibu (3.06 µg/ml) | 71.62 ± 4.38 |

In the case of examples i–iii and viii–xv, one observes the increased cell kill in MRP positive cell lines associated with the combined use of an MRP substrate anti-cancer drug and an NSAID/NSAID derived compound with MRP inhibitory properties.

In example iv one observes the effect of an inactive anti-cancer drug with an active NSAID on the DLKP cell line.

Examples v and vi represent active combinations in accordance with the invention in cell lines expressing resistance mechanisms other than MRP.

Example vii is an example of a metal substrate for MRP and an active NSAID.

Example xvi is an example of an active anti-cancer drug and an inactive NSAID.

It will be observed in the case of the above examples that unless one uses a combination of an MRP substrate and an MRP inhibitor in cells expressing MRP then the increased cell kill is seen to be at best, additive.

EXAMPLE 2

Figure 1:
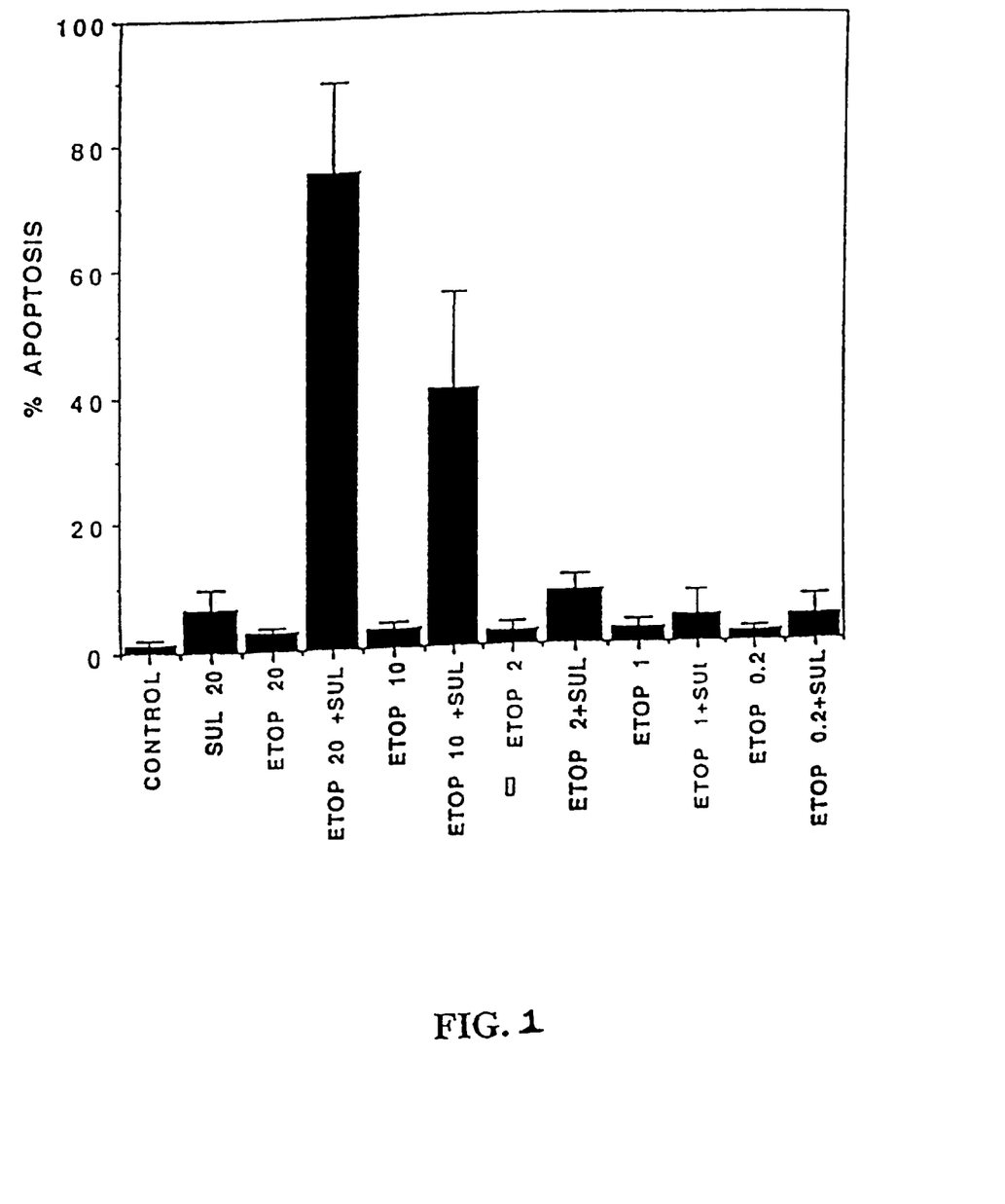
FIG. 1 is a bar graph showing the effect of sulindac on etoposide-induced apoptosis (%) in the cell line HL-60ADR as described in Example 2.
Figure 2:
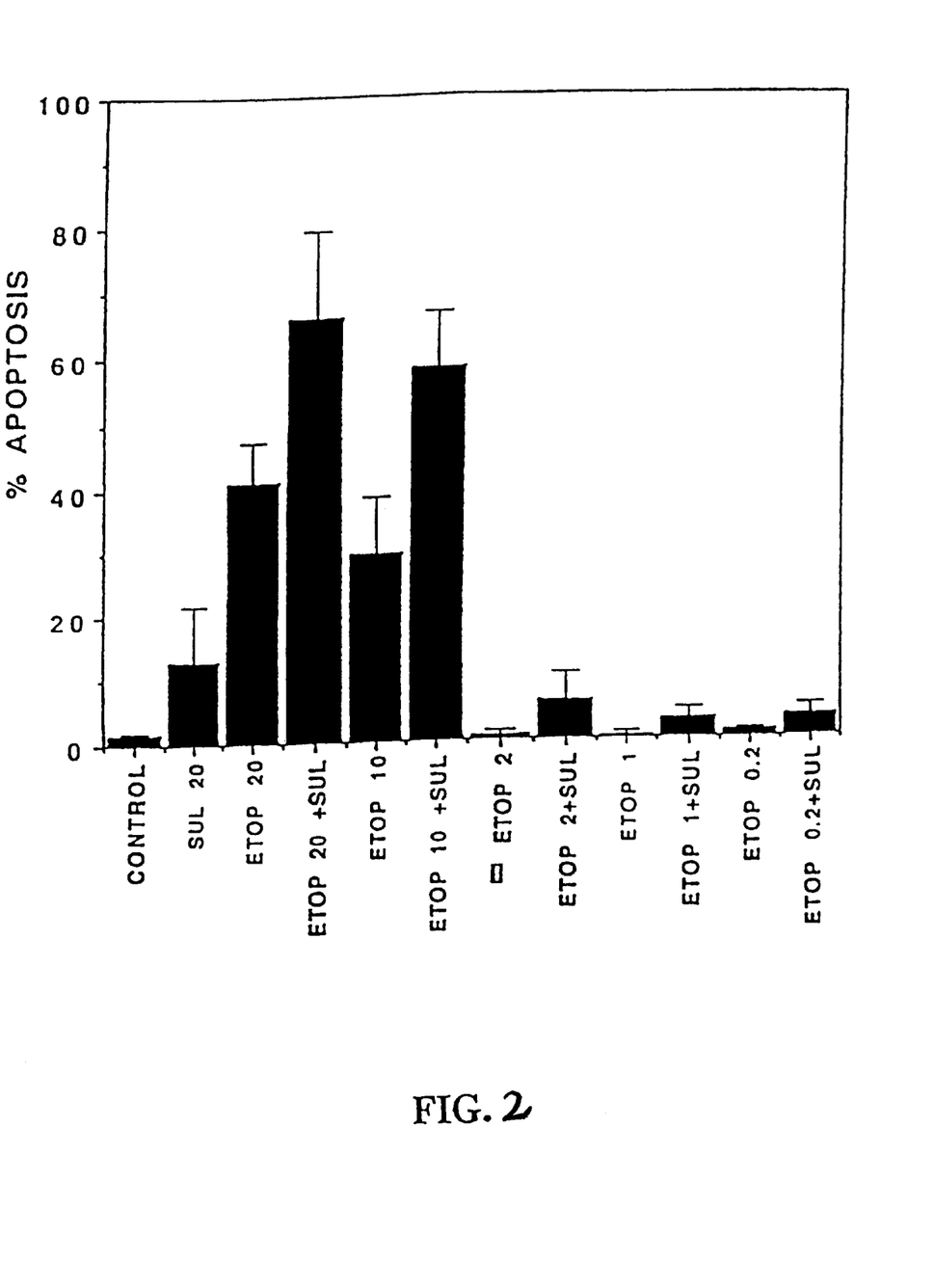
FIG. 2 is a bar graph showing the effect of sulindac on etoposide-induced apoptosis (%) in the cell line HL-60S as described in Example 2.

An experiment was carried out to determine the effect of the NSAID sulindac on etoposide-induced apoptosis in two cell lines, namely HL-60S and HL-60ADR. These cell lines were donated by Dr. Melvin Center, Kansas State University, Manhattan Kans. 66506, U.S.A. For the HL-60S and ADR cell lines the percentage of apoptotic cells within the cell population, following drug exposure, was used to quantify toxicity. Cells were plated in fresh medium at a concentration of $10^6$ cells/ml in a 24-well plate (Greiner) and drugs were then added to the wells. A 200 µl sample from each well was taken after 4 and 8 hrs. Samples were cytospun for 2 min at 500 rpm using a Shandon Cytofuge3. After air-drying the cytospins were stained using a Romanowsky staining kit, Rappi-Diff II (Langanbach), dried and mounted in DPX (BDH). Slides were studied on an Optiphot microscope (Nikon) fitted with a 40× objective, and visualised on a monitor via a Mitsubishi CCD-100E colour CCD-camera and a 0.6× relay lens. Nuclear fragmentation was used as a morphological marker for apoptosis and a minimum of 200 cells were assessed in at least three different microscopic fields. Results were expressed as the percentage of apoptotic cells within the population. Each experiment was repeated in duplicate. The results are shown in FIGS. 1 and 2.

When treated with etoposide only a basal level of apoptosis is seen in the resistant HL-60ADR cells as compared with the sensitive HL-60S line. However, when HL-60ADR cells are co-treated with sulindac, a significant increase in the amount of cells dying by apoptosis is observed. In HL-60S the increased apoptosis is only due to an additive effect of both etoposide and sulindac.

EXAMPLE 3

An experiment was carried out to determine the effect of doxorubicin in combination with sulindac on cell lines with and without MRP as described below.

Doxorubicin, daunorubicin (internal standard) and sulindac were obtained from Farmitalia Carlo Erba Ltd. (UK), Rhone-Poulenc Rorer (UK) and Sigma Chemical Co. (UK) respectively. Sulindac was dissolved in DMSO and diluted to the appropriate concentration in culture medium, namely <0.1% which was non-toxic in the assays used.

Cell Treatment $10^6$ COR L23 P (parental non-MRP resistant, MRP−) or COR L23 R (MRP resistant, MRP+) cells were added to 75 cm³ vented flasks containing HEPES buffered Rosemount Park Memorial Institute (RPMI) medium and maintained at 37° C. in a 5% $CO_2$ atmosphere. COR L23 cells were a gift from Dr. Peter Twentyman, MRC Clinical Oncology Unit, Cambridge CB2 2QH, England. After three days of growth, doxorubicin (final concentration 10 mg/ml), sulindac (final concentration 20 mg/ml) or doxorubicin and sulindac were added to individual flasks. Samples were taken after 1, 2 and 4 h. and assayed for drug content.

Drug Extraction

The contents of each flask were washed twice with 5 ml of PBS and stored at −70° C. The flasks were thawed and 100 µl of water and 100 µl of 33% silver nitrate added to each and mixed for 5 min. 300 µl of methanol (containing 5 µg of daunorubicin as an internal standard (I.S.)) and 1.3 ml of acetonitrile were then added and the flasks mixed for 5 min. The mixture was transferred to glass tubes and refrigerated for 1 hr., The tubes were centrifuged at 4000 rpm and 1.1 ml of the clear layer removed to high performance liquid chromatography (HPLC) autosampler vials. The solvent was evaporated off at room temperature under a stream of nitrogen gas.

HPLC Analysis

The extract was resuspended in 50 µl of methanol in the sample vial and loaded into the HPLC autosampler. The HPLC system comprised a Beckman System Gold 507 autosampler, 125 pump and 166 detector. 20 µl of the reconstituted sample was automatically injected into the HPLC system. The HPLC analysis conditions consisted of 2 mobile phases. Mobile phase 1 consisted of 32 ml of 0.1 M phosphoric acid and 244 ml of ultrapure water. This was mixed and the pH adjusted to 2.3 with a few drops of potassium hydroxide. 124 ml of HPLC grade acetonitrile was added and the mixture was degassed by sonication in a sonicating bath for 5 min. The second mobile phase consisted of HPLC grade acetonitrile. The mobile phases were pumped through a C18 reversed-phase Ultrasphere XL (Beckman) HPLC column (4.6×70 mm) with absorbance measured at 253 nm. For the first 14 min. of the chromatographic run mobile phase 1 was pumped through the column at 0.33 ml/min. From 14 to 20 min. mobile phase 2 was pumped through the column. The column was switched back to m.p. 1 at 20 min. and the flow rate was increased to 0.66 ml/min at 22 min. At 30 min. the flow rate was brought back to 0.33 ml/min. The run continued for a further 5 min. The amount of doxorubicin and sulindac present was quantified by measuring the peak height of these drugs and the internal standard. The peak height of the doxorubicin peak was divided by that of the IS and the ratio plotted against concentration for a series of doxorubicin concentrations. The concentration of doxorubicin in the samples was calculated from the) nd development standard line using the peak height ratio. The sulindac concentrations were calculated by the same method. The results are shown in FIGS. 3 and 4.

Figure 3:
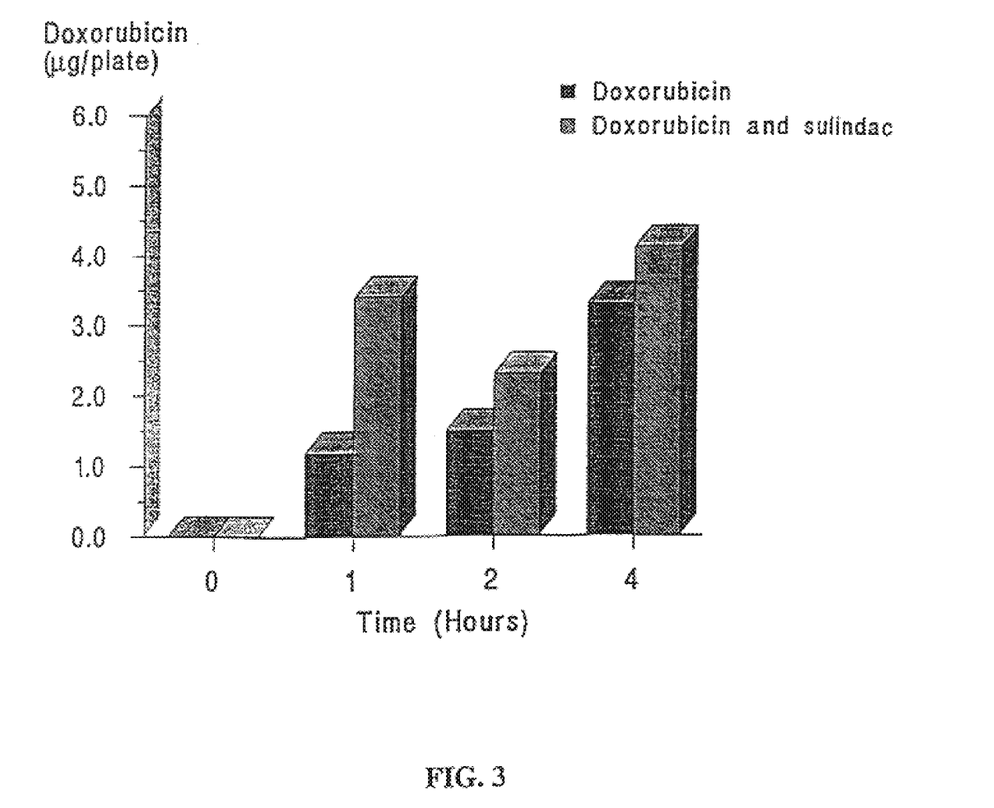
FIG. 3 is a bar graph showing doxorubicin levels in COR L23 R (MRP+) cells alone or in combination with sulindac versus time (hours) as described in Example 3.
Figure 4:
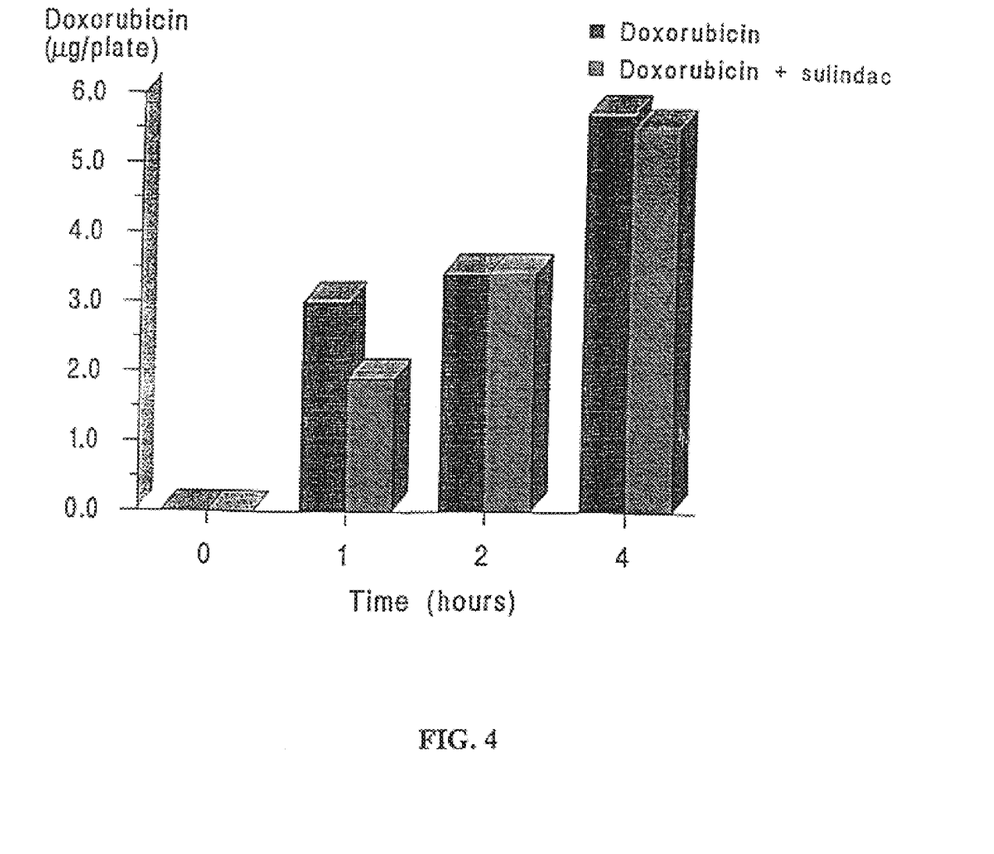
FIG. 4 is a bar graph showing doxorubicin levels in COR L23 P (non-MRP) cells versus time (hours) as described in Example 3.

As will be observed from FIGS. 3 and 4 in the MRP—cell line high levels of doxorubicin are found in the cell regardless of the co-treatment with sulindac. With the MRP+cells, less doxorubicin is found in the cells. When sulindac is co-administered, the doxorubicin level in the cells is increased to near that found in the MRP—cells.

EXAMPLE 4

The expression of the MRP pump was investigated in the cell lines used in Examples 1–3 using Western blotting techniques. A commercially available antibody (obtained from TCS Biologicals Ltd., Botolph Claydon, Buckingham MK18 12LR England), MRP-r1 was used to probe cellular extracts immobilised onto a nitrocellulose membrane. Table 1 below shows which cells were found to be positive. The level of protein found varied from none in two of the sensitive cells (−), a proportionately small amount ((+)) in the DLKP cells and a large amount (++) in the COR L23 R cells.

TABLE 1

| Cell Line | MRP status |
| --- | --- |
| HL60 (S) | − |
| HL60 (ADR) (drug resistant) | + |
| COR L23 (S) | − |
| COR L23 (R) (drug resistant) | ++ |
| DLKP | (+) |

EXAMPLE 5

Additional cell toxicity assays were undertaken using anti-cancer drugs from two of the positive classes of chemotherapeutics, epirubicin, an anthracycline, and teniposide, an epipodophyllotoxin, in combination with the positive NSAIDs sulindac and indomethacin, respectively.

For the monolayer cell lines miniaturised in vitro assays were used to determine drug toxicity. On Day I cells were seeded at $1 \times 10^3$ cells/well in a 96-well plate and left to attach overnight. Drug was added on Day 2, and the assay was terminated on Day 7. Cell number was then evaluated by using one of two colorimetric end-point asssays: the acid phosphatase assay (Martin, A., and Clynes, M. (1991); In vitro Cell and Development Biology, 27A: 183–184) or the crystal violet dye elution assay (Martin, A., and Clynes, M. (1993); Cytotechnology, 11:49–58). All assays were performed in triplicate. The results are shown in Table 2.

TABLE 2

Demonstration of synergistic combinations of epirubicin with sulindac and teniposide with indomethacin in DLKP cells.

| Epirubicin (Epi) (1 ng/ml) | 69.08 ± 3.6 |
| --- | --- |
| Sulindac (Sul) (1.5 µg/ml) | 99.92 ± 3.3 |
| Epi ± Sul (1.5 µg/ml) | 32.01 ± 5.8 |
| Sul (3.0 µg/ml) | 100.29 ± 3.2 |
| Epi ± Sul (3.0 µg/ml) | 16.15 ± 2.0 |
| Sul (6.0 µg/ml) | 100.07 ± 3.6 |
| Epi ± Sul (6.0 µg/ml) | 11.46 ± 0.9 |
| Teniposide (Ten) (6.25 ng/ml) | 79.79 ± 0.97 |
| Indomethacin (Indo) (0.6 µg/ml) | 102.06 ± 5.11 |
| Ten + Indo (0.6 µg/ml) | 63.01 ± 0.59 |
| Indo (1.25 µg/ml) | 101.28 ± 5.12 |
| Ten + Indo (1.25 µg/ml) | 55.54 ± 1.15 |
| Indo (2.5 µg/ml) | 96.18 ± 3.43 |
| Ten + Indo (2.5 µg/ml) | 54.09 ± 0.79 |

The data in Table 2 is expressed as % cell survival ±S.D. for a minimum of 3 determinations. In all cases the NSAIDs were used at non-toxic concentrations (Cell Survival >95%). The results show that the combination of the anticancer agents, epirubicin or teniposide, plus sulindac or indomethacin gives a greater cell kill than would be anticipated by adding the individual cell kills for each agent in the combination.

Thus, the results show a dose dependent synergy in the combination and suggest that other members of these two chemotherapeutic drugs may also have the potential for synergistic activity.

EXAMPLE 6

The expression of MRP in the drug-sensitive cell lines was analysed using Western blotting techniques to probe for the presence of the MRP protein. Western blotting for MRP detection was performed using whole cell extracts, except for DLKP cells for which a plasma membrane vesicle preparation was used. The protein concentration of each fraction was estimated by the Pierce Bincinchoinic acid (BCA) protein assay (Smith, P., et al., (1985); Anal. Biochem., 150: 76–85). The proteins were separated using 7.5% SDS-polyacrylamide gels in a discontinuous buffer system according to the method of Laemmli, U.K., (1970); Nature, 227: 680–685. Western blotting was performed by the method of Towbin, H., et al. (1979); Proc. Natl. Acad. Sci., 76 :4350–4354, using PVDF western blotting membranes (Boehringer Mannheim). Following protein transfer the nitrocellulose sheets were placed in blocking buffer (5% non-fat dried milk in Tris buffered saline (20 mM Tris, 500 mM NaCl, pH 7.5) for 2 hours prior to addition of the primary antibody. The primary antibody used was an anti-human MRP monoclonal, Clone MRPr1, from TCS Biologicals. The secondary antibody was a horseradish peroxidase-linked antibody from Dako, which was detected by ECL (Amersham). The results are shown in Table 3.

TABLE 3

MRP status of selected cell lines as indicated by Western Blot analysis.

| Cell line | MRP Status |
|---|---|
| COR L23P | − |
| COR L23R | + |
| A549 | + |
| DLKP (Plasma membrane vesicle prep.) | + |
| COR L23 R (Plasma membrane vesicle prep.) | ++ |

Table 3 shows that expression of MRP was observed in DLKP, A549, and COR L23R cells. The level of the MRP protein varied from none in the sensitive cell line COR L23P to a large amount in the COR L23 R (MRP-resistant) cells. In the case of DLKP a plasma membrane preparation from the cells was used, instead of the usual total cell lysate, to aid in the visualisation of the result.

EXAMPLE 7

To determine if the NSAIDs were acting directly on the MRP pump the uptake of [$^3$H]LTC$_4$ into inside-out plasma membrane vesicles prepared from HL60ADR cells was examined using a rapid filtration procedure (Ishikawa,T., et al. (1994); J. Biol. Chem. 269 (46); 29085–29093). ATP-dependent transport of [$^3$H]LTC$_4$ into the membrane vesicles was measured by a rapid filtration method using a Millipore sampling manifold. The membrane vesicles were thawed at 37° C. before use and kept on ice. The reaction components consisted of 0.25 M sucrose/10 mM Tris.HCl pH 7.4/1 mM ATP/10 mM MgCl$_2$/10 mM creatine phosphate/ 110 μg/ml creatine kinase and 10 nM [$^3$H]LTC$_4$, with 50 μg of the inside-out vesicle preparation, in a final volume of 110 μl. This suspension was incubated at 37° C., with gentle mixing, and aliquots, 20 μl, were taken at the indicated points. Those aliquots were diluted in 1 ml of ice-cold incubation buffer before being applied to 0.22 μm Millipore GSWP nitrocellulose filters, pre-soaked in ice-cold incubation buffer, under suction. The filters were subsequently washed with 3 ml ice-cold incubation buffer, and absorbed radioactivity was measured using a scintillation counter (Beckman). In control experiments ATP was replaced with 5μ-AMP to determine the ATP-dependent transport. The results are shown in Table 4.

TABLE 4

Effect of selected NSAIDs on transport of [$^3$H]LTC$_4$ into inside-out vesicles from HL60ADR cells.

| NSAID | Concentration | % inhibition |
|---|---|---|
| None | — | 0% |
| Indomethacin | 98 μM | 70% |
| | 49 μM | 20% |
| Sulindac | 89 μM | 69% |
| | 45 μM | 25% |
| Tolmetin | 0.863 mM | 50% |
| | 0.432 mM | 22% |
| Naproxen | 2.2 mM | 15.5% |
| Piroxicam | 0.302 mM | 0% |

The data in Table 4 suggests that the positive NSAIDs, especially sulindac and indomethacin, have MRP-pump inhibitory activity whereas inactive NSAIDs, naproxen and piroxicam, do not.

EXAMPLE 8

MRP is an extremely efficient transporter of glutathione conjugates and it has been suggested that glutathione metabolism is an important factor in drug-efflux from MRP over-expressing cell lines (Versantvoort, C. H. M., et al, (1994); Biochem. Pharmacol., 48: 1129–1236) Furthermore, indomethacin has been shown to be an inhibitor of GSTs (Hall, A., et al, (1989); Cancer Res., 49: 6265–6268; Mosialou, E., and Morgenstern, R., (1990); Chem. Biol. Interactions, 74: 275–280). The other NSAIDs were tested in a total GST assay (Habig, W. H., and Jakoby, W. B., (1981); Methods Enzymol., 77: 218–231). Total cellular GST activity was assayed, using 1-chloro-2,4-dinitrobenzene as a substrate, according to the method of Habig, W. H., and Jakoby, W. B., (1981); supra. Due to spectrophotometric interference at 340 nm, caused by the majority of the NSAIDs, the assays were all performed at 360 nm, without any apparent effect on the rate of the control reaction The results are shown in Table 5.

TABLE 5

Effect of NSAIDs on GST prepared from DLKP cells. Data are expressed as % inhibition of control (100%) ± S.D. for a minimum of 3 determinations.

| NSAID | Concentration (mM) | % Inhibition* |
|---|---|---|
| Acemetacin | 0.25 mM | 58% |
| Zomepirac | 0.25 mM | 56% |
| Sulindac | 0.25 mM | 42.6% |
| Tolmetin | 0.4 mM | 55% |
| Indomethacin | 0.4 mM | 54% |
| Diclofenac | 0.75 mM | 54% |
| Flufenamic Acid | 0.75 mM | 41.2% |
| Fenoprofen | 1 mM | 22.5% |
| Ibuprofen | 1 mM | 18.5% |
| Naproxen | 1 mM | 17% |
| Fenbufen | 1 mM | 15.6% |
| Ketoprofen | 1 mM | 11.2% |
| Levamisole | 1 mM | 0% |

The data in Table 5 suggest that the NSAIDs do possess GST inhibitory ability but at concentrations that are higher than listed serum concentrations for these drugs.

EXAMPLE 9

To further investigate if the effect we describe was due to MRP, experiments were undertaken to measure the cellular concentration of adriamycin after a loading dose with no NSAID, an NSAID negative in our screen (piroxicam) and a positive NSAID indomethacin.

The level of adriamycin within the indomethacin treated cells remained constant during the 4 hours of the experiment, whereas in the control and piroxicam treated cells the level of adriamycin in the cells gradually decreased. DLKP-7 cells were seeded into 75 cm$^2$ flasks at 0.5×10$^6$ cells/10 ml ATCC medium. The cells were left for 2 days, the ATCC medium was removed and fresh medium containing adriamycin (0.5 μg/ml) was added. Following a 2 hour incubation this medium was removed, the flasks were washed twice with PBS, 10 ml ATCC medium or ATCC medium containing the test NSAID was added, and the cells were incubated for a further 4 hr. The cells were trypsinised and the pellet was frozen at −20° C. Duplicate flasks for each time point were prepared. The NSAIDs used were indomethacin 10 μg/ml and piroxicam 20 μg/ml.

The amount of adriamycin in the cells was quantified using liquid-liquid extraction and reverse-phase HPLC analysis. The frozen cell pellets were thawed and resuspended in 100 µg of water/100 µl of 33% silver nitrate and mixed for 5 min. 300 µl of methanol, containing 1.5 µg of daunorubicin as an internal standard (IS), and 1.3 ml of acetonitrile were then added and the tubes mixed for a further 5 min. The mixture was transferred to glass tubes and kept at 4° C. for 1 hr. The tubes were then centrifuged at 1000 g for 15 min. to pellet any solid material. 1.1 ml of the supernatant was removed to HPLC autosampler vials (Labquip, Dublin, Ireland). The solvent was evaporated off at room temperature under a stream of nitrogen gas.

The extract was resuspended in 50 µl of mobile phase 1 (MP1): 32 ml of 0.1 M phosphoric acid mixed with 244 ml of ultrapure water, pH: 2.3 (adjusted upwards with a few drops of 1N potassium hydroxide) to which 124 ml of acetonitrile was added and the final mixture was degassed in a sonicating bath for 5 min. The second mobile phase (MP2) consisted of acetonitrile. The resuspended sample (20 µl) was automatically injected into the HPLC system. The HPLC system comprised a Beckman System Gold 507 autosampler, 125 pump and 166 detector. The MP was pumped through a C18 reversed-phase Prodigy 5 µm particle size ODS-3 column (Phenomenex, Macclesfield, England) (dimensions 150×4.6mm) and absorbance was measured at 253 nm. For the first 14 min. of the chromatographic run MP 1 was pumped at 0.5 ml/min. From 14 min. to 20 min. the column was switched to MP 2. At 20 min. the column was switched back to MP 1 and the flow rate increased to 1 ml/min. At 30 min. the flow rate was brought back to 0.5 ml/min. The run continued for a further 5 min. giving a total run time of 35 min. The amount of adriamycin present was quantified by measuring its peak area and the peak area of the IS. The peak area of the adriamycin was divided by the area of the IS peak and the ratio plotted against a concentration series for spiked adriamycin samples. The results are shown in Table 6.

TABLE 6

Inhibition of adriamycin efflux from cells treated with indomethacin relative to untreated and piroxicam treated cells.

| NSAID | % Adriamycin content at 0 h | % Adriamycin content at 4 h |
|---|---|---|
| Control | 100 | 64 ± 5 |
| Piroxicam | 100 | 67 ± 10 |
| Indomethacin | 100 | 109 ± 4 |

The results demonstrate that export of adriamycin from MRP—expressing cells can be inhibited by indomethacin.

EXAMPLE 10

The in vivo relevance of our findings was studied using a mouse tumour model. SP2 tumour cells were injected into 4 groups of mice. Groups of 8 male Balb/c mice 8 weeks old were maintained on normal diets. Animals were injected with 2 million SP2 mouse myeloma cells on day 1. On day 3 intraperitoneal injection with adriamycin, tolmetin or a combination of the two was begun. This continued once a day, five days a week for a total of 32 days. The agents were dissolved in PBS and prepared freshly twice per week. The animals were weighed and the average weight of the group was used to calculate the required concentration of the drugs. Adriamycin was administered to give a final concentration of 0.25 mg/kg, the tolmetin dose was 70 mg/kg. Animals were exsanguinated when they showed signs of distress or tumours grew above the required size (20 mm in any one axis). The results were expressed as the number of animals alive each day as a percentage of the original number of animals alive.

Figure 5:
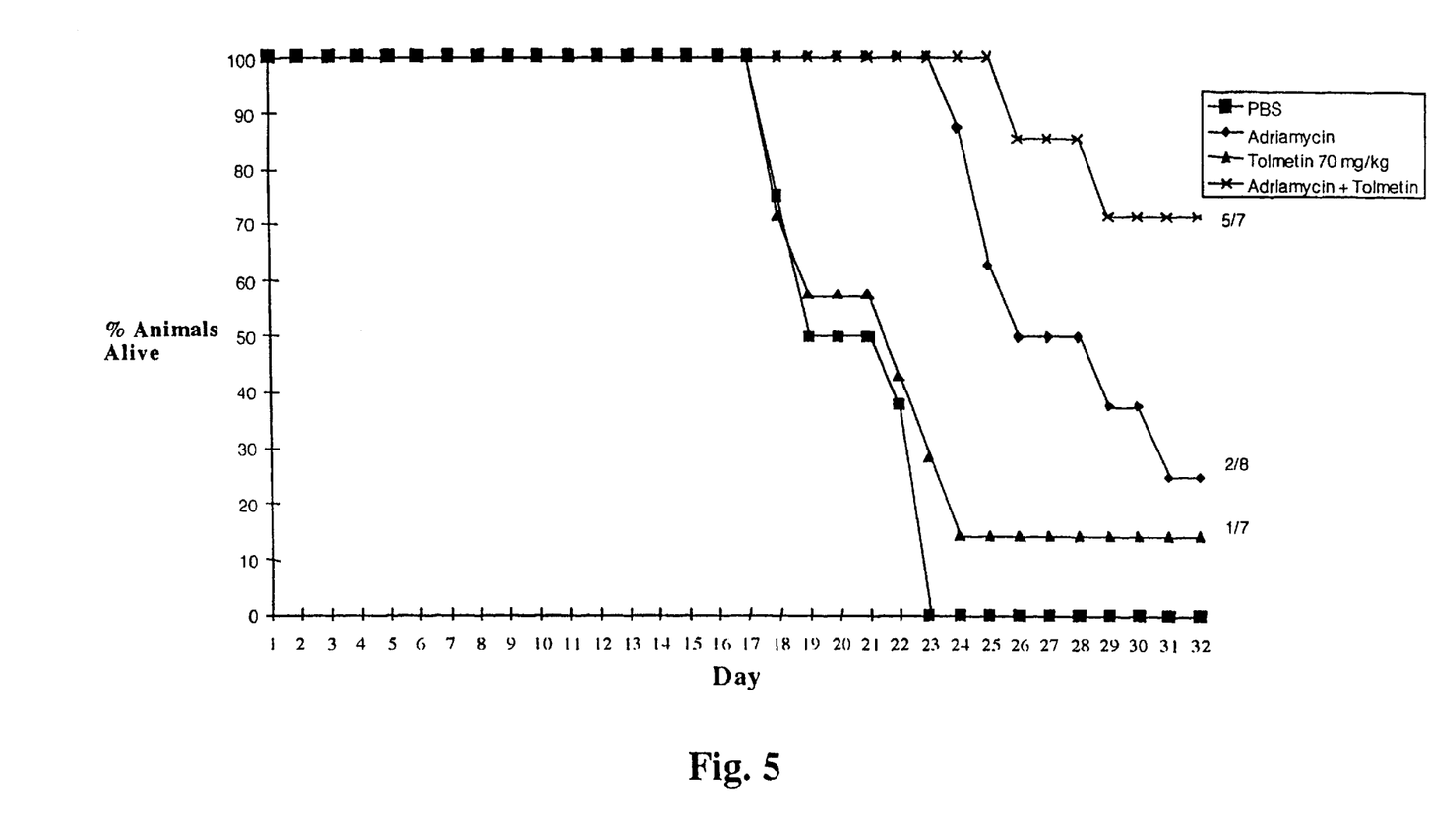
FIG. 5 is a graph showing the survival curves of Balb/c mice injected intraperitoneally with 2 million SP2 cells over 32 days of treatment. The treatment groups are as indicated.

Group 1 received injections of the vehicle (PBS) alone, group 2, adriamycin at 0.25 mg/kg, group 3, tolmetin at 70 mg/kg and group 4 received both agents (adriamycin, 0.25 mg/kg and tolmetin, 70 mg/kg). After 32 days there were clear differences in the % survival between the groups (FIG. 5). All mice from group 1 and all but one from group 3 were dead. Two mice remained in the adriamycin group but 5 survived to the end of the experiment from the combination group (group 4). These results show a superior effect of the combination of tolmetin and adriamycin to that seen with the anti-cancer agent alone against a tumour growing in vivo.

What is claimed is:

1. A method of increasing the cytotoxicity of a substrate of multidrug resistance related protein (MRP) in a subject, which comprises administering simultaneously, sequentially or separately to said subject a non-steroidal anti-inflammatory drug (NSAID) having MRP inhibitory activity in an amount effective to inhibit MRP, with the proviso that when the substrate for MRP is etoposide, the NSAID is other than indomethacin.

2. A method of overcoming resistance to chemotherapy in a subject being treated with a substrate of MRP, which comprises administering simultaneously, sequentially or separately to said subject a non-steroidal anti-inflammatory drug (NSAID) having MRP inhibitory activity in an amount effective to inhibit MRP, with the proviso that when the substrate for MRP is etoposide, the NSAID is other than indomethacin.

3. The method according to claim 1 or 2, wherein the substrate is an anti-cancer drug.

4. The method according to claim 1 or 2, wherein the substrate is an anti-cancer drug selected from the group consisting of an anthracycline, a vinca alkaloid and an epipodophyllotoxin.

5. The method according to claim 1 or 2, wherein the substrate is an anti-cancer drug selected from the group consisting of anthracycline adriamycin, daunorubicin and epirubicin.

6. The method according to claim 1 or 2, wherein the substrate is vinca alkaloid vincristine.

7. The method according to claim 1 or 2, wherein the substrate is an anti-cancer drug selected from the group consisting of epipodophyllotoxin etoposide (VP-16) and teniposide.

8. The method according to claim 1 or 2, wherein the substrate is a transition metal complex.

9. The method according to claim 1 or 2, wherein the NSAID is a heteroarylacetic acid.

10. The method according to claim 1 or 2, wherein the NSAID is selected from the group consisting of acemetacin, indomethacin, sulindac, sulindac sulfide, sulfindac sulfone, tolmetin and zomepirac.

11. A method of increasing the cytotoxicity of a substrate of multidrug resistance related protein (MRP) in a subject, which comprises administering simultaneously, sequentially or separately to said subject, using oral, intravenous, intra-arterial or intramuscular administration, a non-steroidal anti-inflammatory drug (NSAID) having MRP inhibitory activity in an amount effective to inhibit MRP, with the proviso that when the substrate for MRP is etoposide, the NSAID is other than indomethacin.

12. A method of overcoming resistance to chemotherapy in a subject being treated with a substrate of MRP, which comprises administering simultaneously, sequentially or separately to said subject, using oral, intravenous, intra-arterial or intramuscular administration, a non-steroidal anti-inflammatory drug (NSAID) having MRP inhibitory activity in an amount effective to inhibit MRP, with the proviso that when the substrate for MRP is etoposide, the NSAID is other than indomethacin.

13. The method according to claim 11 or 12, wherein the substrate is an anti-cancer drug.

* * * * *